United States Patent [19]
Vassarotti

[11] Patent Number: 5,647,990
[45] Date of Patent: Jul. 15, 1997

[54] CENTRIFUGAL METHOD FOR CONCENTRATING MACROMOLECULES FROM A SOLUTION AND DEVICE FOR CARRYING OUT SAID METHOD

[76] Inventor: Vincenzo Vassarotti, Au Village, Bugnaux sur Bolle, Switzerland, CH-1180

[21] Appl. No.: 374,594

[22] PCT Filed: May 24, 1994

[86] PCT No.: PCT/EP94/01701

§ 371 Date: Jan. 20, 1995

§ 102(e) Date: Jan. 20, 1995

[87] PCT Pub. No.: WO94/27724

PCT Pub. Date: Dec. 8, 1994

[30] Foreign Application Priority Data

May 21, 1993 [SE] Sweden ................................. 9301759

[51] Int. Cl.$^6$ ...................... B01D 21/26; B01D 61/00
[52] U.S. Cl. .................. 210/650; 210/781; 210/380.1; 210/407; 422/72; 422/101; 436/177
[58] Field of Search .................... 210/650, 781, 210/380.1, 407, 500.21, 514; 422/72, 101; 436/177

[56] References Cited

U.S. PATENT DOCUMENTS

| | | | |
|---|---|---|---|
| 3,488,768 | 1/1970 | Rigopulos | 210/409 |
| 3,583,627 | 6/1971 | Wilson. | |
| 4,632,761 | 12/1986 | Bowers et al. | 210/650 |
| 4,722,792 | 2/1988 | Miyagi et al. | |
| 4,874,516 | 10/1989 | Kondo | 210/500.21 |
| 4,919,860 | 4/1990 | Schindler et al. | 210/500.21 |

FOREIGN PATENT DOCUMENTS

| | | |
|---|---|---|
| 430355 | 6/1991 | European Pat. Off. . |
| 2371225 | 6/1978 | France . |
| 8900289 | 1/1989 | WIPO . |

*Primary Examiner*—David A. Reifsnyder
*Attorney, Agent, or Firm*—Mark P. Stone

[57] ABSTRACT

A method and device for concentrating macromolecules from a solution is provided by spinning a concentrated device in a centrifuge. The device has a sample reservoir (1) for receiving a sample to be concentrated or purified, a filter for filtering the sample, a centrifuge tube (5) for collecting the filtrate, and a concentrate pocket (4) for retaining the concentrate. A portion of the sample reservoir (1) is a filtration chamber (3) having a volume which is only a small fraction of the total volume of the sample reservoir. The filter is arranged in a sidewall of the filtration chamber, and the concentrate pocket (4) is arranged in a bottom wall of the filtration chamber. Liquid sample is placed in the sample reservoir, and a unit including the sample reservoir (1) and the filter (2) is placed, at least partially, into the centrifuge tube for collecting the filtrate. As a result of centrifugal force, a force vector is created acting on the macromolecules and sweeping the filter surface, and the macromolecules are collected in the concentrate pocket (4) away from the filter surface.

29 Claims, 3 Drawing Sheets

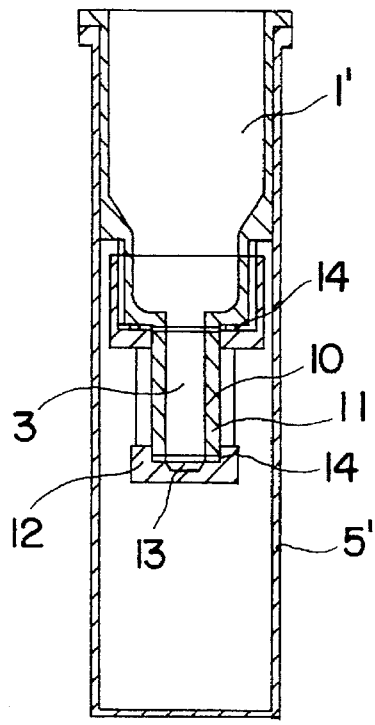
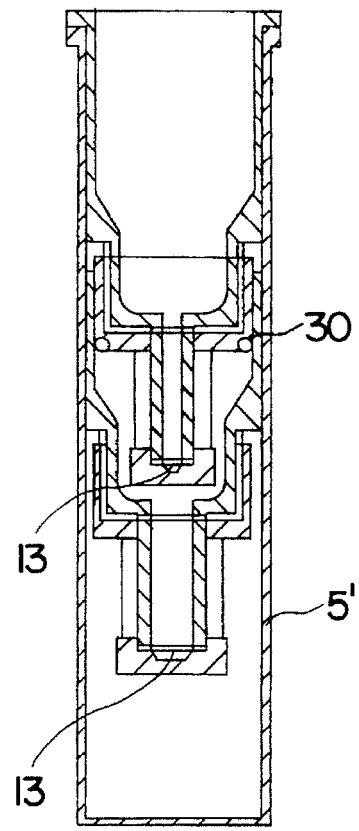
FIG. 5  FIG. 6
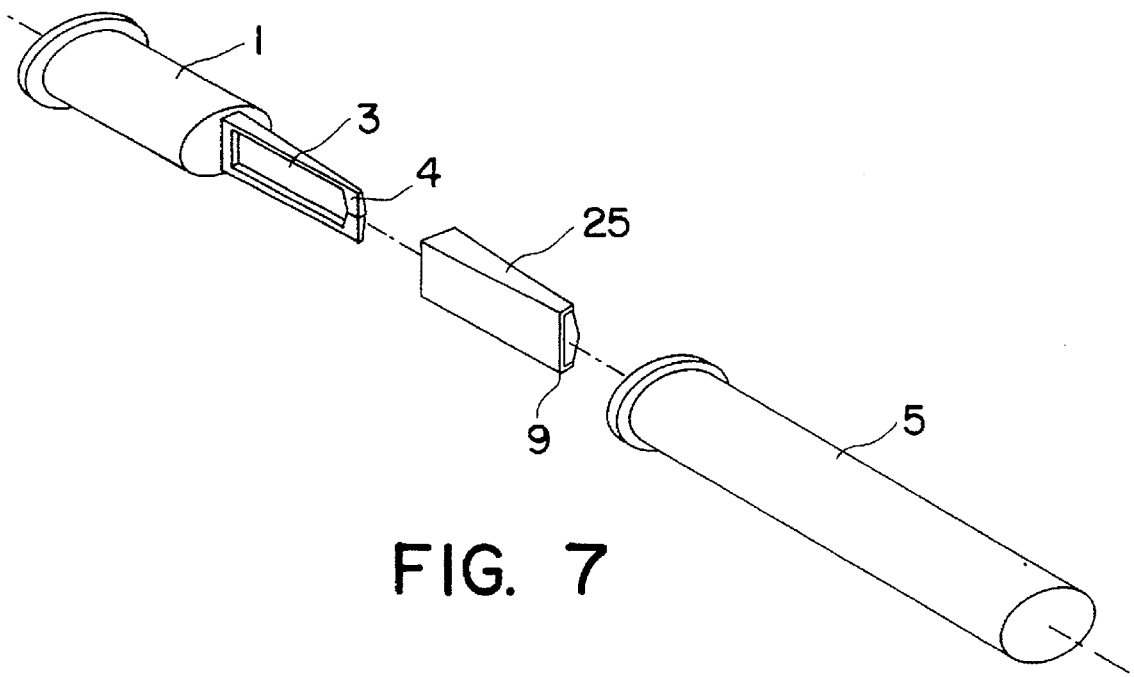
FIG. 7

CENTRIFUGAL METHOD FOR CONCENTRATING MACROMOLECULES FROM A SOLUTION AND DEVICE FOR CARRYING OUT SAID METHOD

This invention relates to centrifuge methods and devices for concentrating macromolecules from a solution.

There has been a number of analytical procedures developed in the biochemical art wherein it is required to remove solvent from e.g. protein solutions in order to have a more concentrated protein sample which can be analysed effectively, or in order to have a protein free filtrate for analysis, or to replace or remove low molecular weight ions or solutes, or to study protein binding attributes of various chemicals in combination with various protein samples. Many other analytical procedures involving not only proteins but macromolecular species in general, have also been developed wherein it is necessary to concentrate a macromolecular component in a liquid sample.

When concentrating small volumes of macromolecules in solution using filtration, e.g. ultrafiltration, there exist the problems of macromolecular binding to the membrane surface and of filtration to dryness. If part of the retentate is adsorbed on the membrane surface the yield of the process will of course decrease and the filtration time will increase due to the decreasing effective membrane area.

In the design of centrifugal filtration devices, the effective membrane area to sample volume to be filtered has been limited by the designs proposed. Low membrane area to volume ratios provide good recovery but low filtration rates. Conversely low volume and large membrane surfaces result in faster filtration but lower recoveries due to the protein binding to the membrane surface.

In the prior art, the centrifugal self-cleaning ultrafilter, described in U.S. Pat. No. 3,488,768, the teachings of which are incorporated herein, is limited due to the large membrane surface area which causes excessive adsorptive loss of the macromolecules.

The initial advantage of a high flow rate through a large filter surface area is rapidly limited as the concentration goes on and the physical surface area is decreasing. The flow rate through the remaining filter area is also reduced by the effect of concentration polarization.

On the other hand, more recent designs such as AMICON MPS-1 Micropartition system (AMICON Publication 472) and the AMICON CENTRICON device described in U.S. Pat. No. 4,632,761 limits membrane surface area to the area at the bottom of the sample reservoir tube, frequently resulting in a poor ratio of membrane surface area to sample volume and extended concentration time.

The dead stop feature which stops the sample concentrating to dryness according to U.S. Pat. No. 4,632,761 is limited by remaining adsorptive losses which result from the concentrated sample remaining on the surface of the membrane and a reduction of effective membrane surface area resulting from this feature.

To recover the retentate from the concentrate pocket a reverse spinning step is used which means that the centrifuge has to be stopped and the sample reservoir with the filtering means and the centrifuge tube have to be taken out from the centrifuge. The different devices are then rearranged and again inserted into the centrifuge now in a way allowing the centrifugal forces to recover the retentate from the pocket at the bottom of the sample reservoir and the surface of the filter. The use of a pipette to recover the retentate from the bottom of the sample reservoir is delicate because the surface of the filter might be damaged by the tip of the pipette. This necessary step to get the final product out of the concentration device is thus complicated and will take a lot of time. Furthermore, a dedicated retentate recovery tube has to be used which increases the costs.

Whilst the reverse spinning feature partially resolves the problem of loss of recovery on the membrane surface, subsequent loss is caused by the adsorption of the concentrated solution on the membrane and reservoir walls of the apparatus during the reverse spinning procedure.

In addition this device requires a specifically designed filtrate collection vessel which is mounted below the sample reservoir—filter assembly. Typical laboratory centrifuge tubes may not be used which adds costs for using this device.

It is an object of the invention to provide a centrifugal recovery process for the recovery of a maximal amount of concentrated macromolecular retentate without the need for an additional reverse spinning step to free residual particulate matter from the membrane surface and the retentive reservoir.

It is another object of the invention to provide a centrifugal recovery process compatible with a broad range of standard laboratory centrifuge tubes eliminating the need for product specific filtrate vessels.

It is another object of the invention to provide a process which allows the use of both lower cost swinging bucket centrifuge rotors as well as fixed angle versions providing increased flexibility in use.

It is a further object of this invention to provide a centrifugal concentrator which offers a high degree of flexibility in optimizing the relationship between the filtration rate and the decrease of macromolecular recovery caused by large membrane surfaces.

It is another object of the invention to provide a concentrator having a low volume filtration chamber preferably in the form of a thin channel, in the side wall of which the membrane is mounted. The channel being arranged below the main part of the sample reservoir which maximizes sample contact time with the total available membrane surface during concentration.

It is another object of the invention to provide a method which drives particulate matter away from the membrane surface to the concentrate pocket at the bottom of the filtration chamber at an early stage of centrifugation.

It is another object of this invention to provide a concentrator which gives constant final retentate volume in a separate concentrate pocket away from the membrane surface.

It is a still further object of this invention to provide a centrifugal micro volume concentrator that is economical to manufacture.

The problems of the prior art are overcome by the provision of a centrifugal method and a device for carrying out said method as defined in the appended claims.

In one embodiment of the centrifugal filtration system the membrane employed is an ultrafiltration or microfiltration membrane having a maximum pore size of one micron. The membrane could be in sheet form mounted on one or more sides of the filtration chamber. In another embodiment, the membrane is tubular in shape and performs as an integral filtration chamber mounted below the sample reservoir. The membrane is mounted parallel to or within a maximum angle of 35 degrees with respect to the axis of the centrifuge tube. The filtration system could further comprise a thin channel of a maximum of 5 millimeters in the area of the filtration chamber to maintain a constant active membrane surface throughout most of the concentration procedure. This channel is preferably provided with a wider section to facilitate entry with a pipette for concentrate removal. The sample reservoir could be provided with a vented cap to reduce sample evaporation whilst preventing air locking during centrifugation.

In the method of the invention for concentrating macromolecules from a solution without excessive adsorption on the membrane surface and without filtering to dryness, the sample reservoir of the above described novel microconcentrator device is preferably placed in a swinging bucket centrifuge rotor so that during centrifugation the centrifugal force vector sweeps the membrane at an angle in the interval 0°–35° and a concentrated macromolecular final retentate volume is obtained by centrifuging the microconcentrator device until the retentate level falls below the level of the membrane. A retentate reservoir below the membrane surface retains the final retentate solution eliminating the risk of concentrating to dryness.

If an embodiment of the concentrating device with the filter arranged in a window in the side wall of the filtration chamber is used with a fixed angle centrifuge certain combinations of on one hand the angle between the filter and the axis of the centrifuge tube and on the other hand the angle of the centrifuge rotor are especially interesting.

Combinations could be chosen so that the centrifugal force vector sweeps the membrane at an angle of approximately 0°, i.e. parallel to the filter surface, or in a direction away from the filter surface.

The retentate obtained by the method for concentration of macromolecules is preferably recovered by drawing the retentate from the concentrate reservoir by means of a pipette or other recovery device. No reverse spinning step is thus necessary in the method according to the invention.

Other characteristics and advantages of the invention will be apparent from the following description of a few embodiments which will be given with reference to the drawing on which, FIG. 1 is a schematic cross section view of the microconcentrator device fitted into a filtrate recovery tube.

FIG. 5 is a schematic view in partial cross-section of a microconcentration device, using a tubular membrane and membrane support, fitted in a filtrate recovery tube FIG. 6 is a schematic view in partial cross-section of a microconcentration device showing the principle of cascading filter means of the same type as in FIG. 5.

FIG. 7 shows a further embodiment of the invention with a tapered sleeve on the outside of the filtration chamber.

Figure 1:
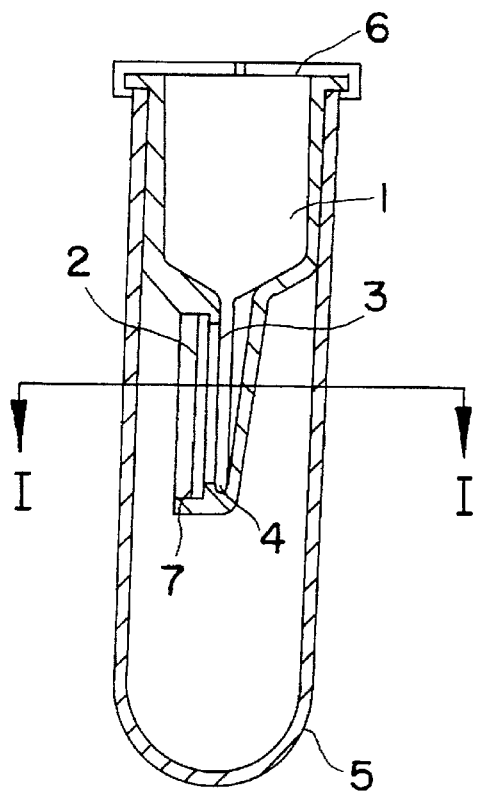

Referring to FIG. 1 there is shown an embodiment of the microconcentrator device of the invention comprising a sample reservoir 1, a membrane and support assembly 2 arranged in the side wall of a filtration chamber 3, which at the lower portion is provided with a retentate reservoir 4 for collecting the concentrate. The assembly is placed in a filtrate recovery tube 5 and a vented cap 6 closes the tube 5. The retentate reservoir is preferably integrated into the design of the filtration chamber 3 and its uppermost edge aligns with the lower edge of the membrane window 7 in such a manner that when filtration is arrested by lack of useful membrane surface the retentate reservoir is full.

Preferably this reservoir is conical in shape to facilitate complete retentate removal and can be varied in size to best suit the concentration level required for different applications. Preferably the retentate reservoir 4 will be sized to allow concentrations of 10 to 300 times of the initial sample volume. The angle between the axis of the sample reservoir, coinciding with the axis of the centrifugal tube, and the flat membrane in the side wall of the filtration chamber can be chosen in the approximate interval 0°–35°.

A big advantage with the device according to the invention is that standard laboratory centrifuge tubes may be used as filtrate collection vessels. The sample reservoir including the filtration chamber may be designed to be put on top of, partly into or completely into the filtrate collection vessel. FIG. 1 shows the embodiment with the sample reservoir and the filtration chamber completely inside the filtrate collection vessel.

Figure 2:
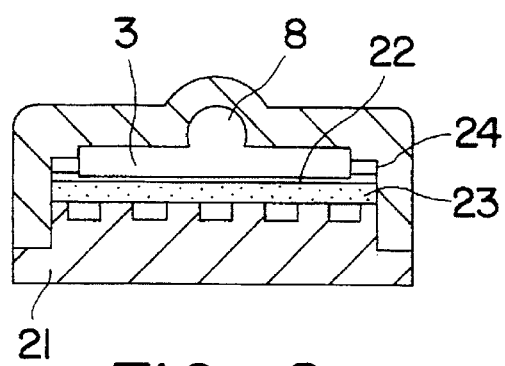
FIG. 2 is a sectional view of the microconcentrator device at the level I—I according to FIG. 1

FIG. 2 shows a cross section of the filtration chamber with a pipette entry port 8, a channelled membrane support plate 21, the membrane 22, a porous sinter membrane support 23, and a membrane gasket 24. The filtration chamber 3 in the form of a flat channel is preferably of a thin section of less than 5 mm to maintain a high membrane surface to volume ratio as the concentration progresses.

If we define a concentration factor as the ratio between the initial sample volume and the final retentate volume the method and device according to the invention can reach much higher values of this factor than the methods and devices according to the prior art. This is due to the feature with a thin channel as filtration chamber and the retentate reservoir away from the filter surface at the bottom of the filtration chamber.

The entry port 8, allows for the removal of the concentrated retentate by means of a pipette. The channelled membrane support plate 21, is sealed to the sample reservoir 1, compressing the gasket 4 against the membrane and thereby providing a liquid tight seal. Any means of sealing may be used such as bonding the membrane directly to the membrane support frame, and thereby eliminating the need for the gasket 4. Similarly, the membrane support plate 23, may be sealed to the sample reservoir 1, by alternative means such as adhesive, heat or chemical bonding, insert moulding and interference fit.

Figure 3:
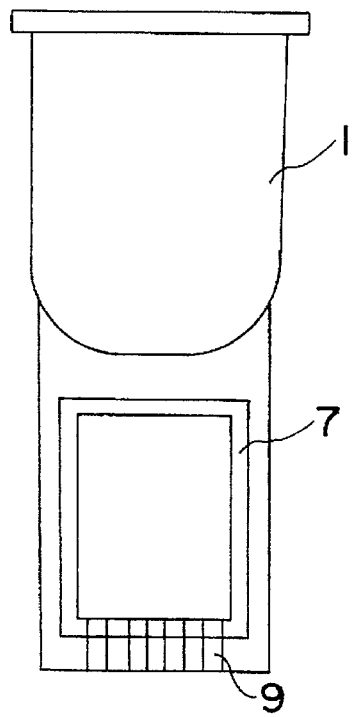
FIG. 3 is a schematic view of the microconcentrator device showing the membrane support frame.

FIG. 3 shows a schematic side view of the device, with the sample reservoir 1, the membrane window 7, and the filtrate outlet channels 9. The window provides for the fitting of the gasket 24, and the membrane 22. The filtrate outlet channels 9, provide for the evacuation of the filtrate from the membrane support to the filtrate recovery tube 5. The membrane window 7, can be sized, depending on the characteristics of the process solution and filtration rate of the membrane to achieve the best compromise between high filtration speed and low adsorption on the membrane surface. When very high filtration rates are necessary, one or more additional membrane windows may be arranged on the other parts of the side wall of the filtration chamber.

Figure 4:
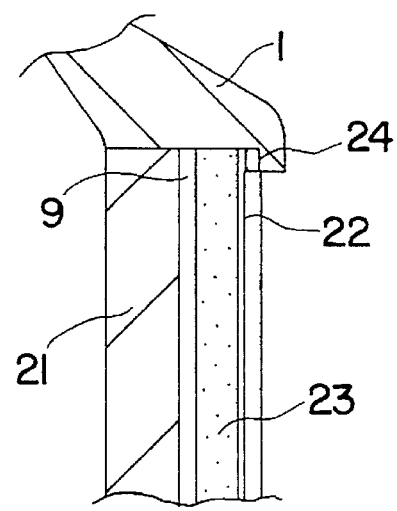
FIG. 4 is a schematic cross section of part of the membrane, membrane support and the joint fixed in the side wall of the concentrator device.

FIG. 4, shows a detail of the membrane assembly with the sample reservoir 1, the membrane support plate 21 with incorporated filtrate outlet channels 9, the gasket seal 24, the membrane 22 and a porous sinter membrane support 23. The porous sinter membrane support 23 is preferably used to provide a more homogeneous support for fragile membranes that could distort into the filtrate outlet channels of the membrane support plate. Any system of filtrate outlet channels may be employed as long as sufficient support is maintained for the membrane and at least one filtrate passage is available to allow filtrate flow from the membrane to the filtrate reservoir 5.

Figure 8:
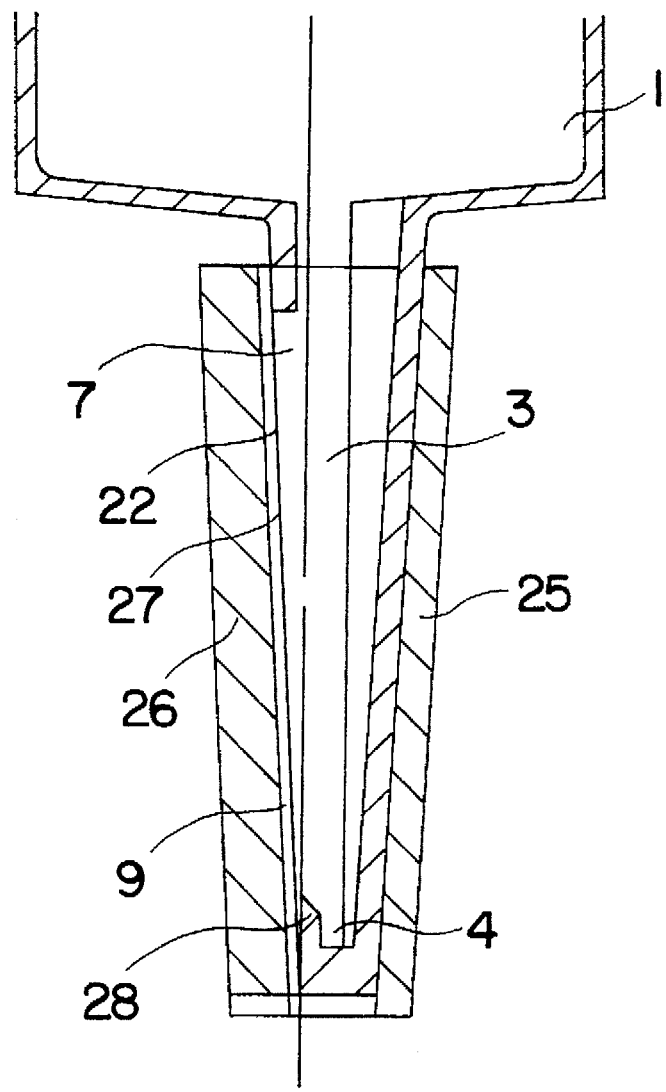
FIG. 8 shows in a sectional view more in detail the essential parts of the embodiment according to FIG. 7.

In an advantageous further embodiment of the invention, cf. FIGS. 7 and 8, the sample reservoir 1 and the filtration chamber 3 including the retentate reservoir 4 form an integral part. The external form of the filtration chamber 3 could e.g. be half a cylinder with the flat surface constituting the membrane window 7. In the illustrations of FIGS. 7 and 8 the actual form of the filtration chamber is tapered in the direction of the retentate reservoir (cf. below). The membrane 22 being fixed by suitable means against the window. On the outside of the filtration chamber 3 a corresponding half cylindrical sleeve 25 is arranged keeping the membrane firmly fixed against the window. The flat side 26 of this half cylindrical sleeve has the role of the membrane support plate 21 in the embodiment described above. This means that the internal flat surface 27 of the sleeve is provided with the filtrate outlet channels 9 in the form of vertical grooves. The vertical position of the sleeve relative to the filtration chamber can be secured by means of cooperating snap-in arrangements (not shown) in the side wall of the chamber and the sleeve.

In a further development of this embodiment the external form of the filtration chamber 3 could be conical or more generally have a tapered form in the direction of the retentate reservoir, as actually shown in the FIGS. 7 and 8. An angle of about 3° for the tapering has been giving excellent results. With a corresponding internal form of the sleeve 25 a very good fixation of the membrane will be possible. It has been shown that the membrane as such does not even have to be fixed against the window by means of glue, heat or the equivalent but will be kept in place tightly against the window by means of the forces exerted by the sleeve when this is slipped over the filtration chamber.

In FIG. 8 another feature of the invention is also shown. For the application with a swinging-bucket rotor the bottom of the reservoir has been arranged at an angle of about 5° to the horizontal, which makes the last part of the volume of the liquid slide down into the filtration chamber or channel.

To allow flow extraction with fixed angle rotors with an angle up to 45° the corresponding angle at the bottom of the sample reservoir would be arranged at about 46°

It could sometimes be of interest during the concentration process to check the volume achieved. The fact that the filtration chamber in the device according to the invention, especially according to FIGS. 1 and 7, has the form of a thin channel containing a very small volume, sometimes in the order of 50 microliters, makes it possible to get an accurate reading of the remaining volume by putting indication markings on the sidewall of the channel or on the outside or inside of the sleeve. It is here assumed that the sleeve as well as the filtration chamber are made of transparent material.

The dead stop feature is realised by means of a partition wall 28 separating the retentate reservoir 4 from the surface of the membrane 22. It could be of advantage to give the cross section of the upper part of this wall the shape of a ramp as shown in FIG. 8 or a trapezoid.

FIG. 5 shows a schematic cross-section of an alternative design for the microfiltration device with the sample reservoir 1', the filtrate recovery tube 5', a tubular membrane 10 supported by means of a porous cylindrical tube 11 forming the side wall of the filtration chamber, a membrane sealing unit 12, with integral retentate reservoir 13 and two sealing gaskets 14, one for each end of the cylindrical tube. In this design the membrane sealing unit is screwed onto the sample reservoir 1' and tightens the sealing gaskets to provide a liquid tight seal between the membrane 10, the sample reservoir 1' and the membrane sealing unit 12. Any other means of sealing may be used including adhesive, heat or chemical bonding or a bayonet assembly. The tubular membrane 10 and its support may be increased or decreased in both diameter and length to achieve the best compromise between a fast filtration speed and minimum adsorption on the membrane surface.

In a further embodiment of the invention, shown in FIG. 6, two or more microconcentrator devices may be stacked in a suitable filtrate recovery tube to sequentially fractionate a sample solution into two or more fractions containing macromolecules of different size. The figure shows a device based on the embodiment according to FIG. 5 with the cylindrical filtration chamber but other types of filtration chambers can alternatively be used. Length and diameter of the filters, i.e filter area, as well as the volume of the retentate reservoir can of course be chosen to suit the actual application. Preferably the successive filter units are screwed on top of each other and sealed from each other so that filtrate will not leak from one reservoir to the other during the handling. In the figure the thread for fastening the second device to the first one is not shown. The sealing is carried out by means of an O-ring 30 but any other appropriate sealing would do. In this process, the uppermost device will be fitted with a more open filter that retains the larger macromolecules but allows passage of smaller macromolecules that will be retained by a filter of lower porosity in the lower device. Depending on the application, up to five or even more devices may be stacked together with sequentially tighter filters. Due to the fact that in fixed angle rotors as well as in swinging bucket rotors the "lower" filters will be spinning at a greater distance from the spinning shaft of the centrifugator the centrifugal forces will be greater in these filters and compensate for the lower flow rate due to the tighter filters.

The fractionated samples may then be collected by means of a pipette individually from the retentate reservoir in each device.

Although any type of semi permeable membrane may be used in the microconcentrator device of the invention, anisotropic membranes, i.e. membranes having an extremely thin microporous barrier layer and a relatively thick macroporous support layer, are preferred and microporous or ultrafiltration membranes characterised by a maximum pore size of one micron has been shown to be most suitable.

The microconcentrator according to the invention is preferably used in a swinging-bucket centrifuge rotor, but the device may also be used in a fixed angle centrifuge rotor. When used in a swinging-bucket rotor the angle between the membrane surface and the direction of the force on the molecules due to the spinning will be approximately 0°, which gives a very good cleaning effect on the membrane surface.

The most common fixed angle rotors use angles of 26–55 degrees. When used in these rotors the angle between the membrane surface of the microconcentrator device and the force vector in the direction away from the membrane will reside in the interval between approximately 35 and 64 degrees which efficiently will keep especially the heavy molecules away from the membrane surface.

Other angles of the fixed rotor could of course be envisaged as well as other angles between the axis of the sample reservoir and the membrane surface in the side wall of the filtration chamber which will result in other sweeping angles for the force vector without leaving the idea of the present invention.

I claim:

1. Method for concentrating macromolecules from a solution by means of spinning a concentrator device in a centrifuge, said device comprising a sample reservoir for receiving a sample to concentrate or purify, filter means for filtering the sample, a centrifuge tube for collecting the filtrate and a particulate concentrate pocket for retention of concentrate, said method comprising the following steps: the liquid sample is put into the sample reservoir, the unit comprising the sample reservoir and the filter means is put into the centrifuge tube for collecting the filtrate so that said filter means and said sample reservoir at least partly are inside said centrifuge tube, the thus created assembly is centrifuged whereby a force vector is created acting on the macromolecules and sweeping the filter surface, the macromolecultes are collected in said particulate concentrate pocket forming a volume of concentrate without contacting the filter surface thereby eliminating the risk of concentration to dryness.

2. Method according to claim 1, comprising the step that said force vector is sweeping the filter surface in a direction parallel to or at an angle oriented in a direction away from at least part of the filter surface.

3. Method according to claim 1, comprising the step that said force vector is sweeping the filter surface in a direction parallel to or at an angle oriented in a direction towards at least part of the filter surface.

4. Method according to claim 2, wherein the angle between said vector and the filter surface is comprised in the interval 0°–75°.

5. Method according to claim 3, wherein the angle between said vector and the filter surface is comprised in the interval 0°–55°.

6. Method according to claim 1, wherein the retentate in the concentrate pocket is recovered by drawing said retentate from the pocket by means of a recovery device.

7. Microconcentrator device for fixed angle and swinging bucket centrifuges, comprising a sample reservoir for receiving a sample to concentrate or purify, filter means for filtering the sample, a centrifuge tube for collecting the filtrate and a particulate concentrate pocket for retention of concentrate, wherein said sample reservoir is provided with a portion constituting a filtration chamber with a volume less than half of the total volume of the sample reservoir, said filtration chamber having a sidewall and a bottom portion, and said filter means being arranged in the sidewall of said filtration chamber and said particulate concentrate pocket being arranged in the bottom portion of said filtration chamber.

8. Microconcentrator device according to claim 7, wherein said filter means is a flat membrane provided with membrane supporting means mounted liquid tight in the side wall of said filtration chamber.

9. Microconcentrator device according to claim 7, wherein the external form of the filtration chamber corresponds to half a cylinder, the filter means being arranged in a flat sidewall of said half cylinder, a corresponding half cylinder sleeve being arranged around said filtration chamber keeping the filter means fixedly against the flat sidewall of said chamber.

10. Microconcentrator device according to claim 7, wherein the filtration chamber defines an external configuration tapered in the direction of the concentrate pocket, the filter means being arranged in at least one flat sidewall portion of said filtration chamber, a sleeve defining an inner configuration adapted to being arranged around said filtration chamber for keeping the filter means firmly fixed against the flat sidewall.

11. Microconcentrator device according to claim 10, wherein said sleeve on the inside is provided with longitudinal grooves forming evacuation channels for the filtrate.

12. Microconcentrator device according to claim 7, wherein said filter means is a membrane curving outward from the filtration chamber provided with membrane supporting means mounted liquid tight in the side wall of said filtration chamber.

13. Microconcentrator device according to claim 7, wherein said filter means is a membrane curving inward into the filtration chamber provided with membrane supporting means mounted liquid tight in the side wall of said filtration chamber.

14. Microconcentrator device according to claim 7, wherein said membrane has a maximum pore size of 1 micrometer.

15. Microconcentrator device according to claim 7, wherein said filter means comprises a cylindrical porous membrane support constituting the said wall of the filtration chamber.

16. Microconcentrator device according to claim 15, wherein said cylindrical membrane support is mounted liquid tight and coaxially with the sample reservoir below said reservoir such that a center axis of said cylindrical membrane support is aligned with a center axis of said sample reservoir.

17. Microconcentrator device according to claim 15, wherein said membrane support is made of a ceramic material.

18. Microconcentrator device according to claim 15, wherein said membrane support is made of a carbon.

19. Microconcentrator device according to claim 15, wherein the membrane is integrally formed on a surface of said membrane support.

20. Microconcentrator device according to claim 15, wherein the membrane comprises a separate cylindrical unit inserted in said membrane support.

21. Microconcentrator device according to claim 7, wherein the bottom of the sample reservoir is funnel-shaped with walls inwardly tapered in the direction of the entry of the filtration channel, said walls being arranged at an angle between 5° and 46° to the direction perpendicular to a central axis of the sample reservoir.

22. Microconcentrtor device according to claim 7, wherein the sidewalls of the channel or an inside or outside portion of the surrounding sleeve is provided with indication markings making it possible to accurately indicate a quantity of liquid volume remaining in the filtration chamber.

23. Microconcentrator device according to claim 7, comprising a partition wall separating the retentate from a surface of the filter means, a cross section of the upper part of said partition wall having the shape of a ramp or a trapezoid.

24. Microconcentrator device according to claim 7, wherein said filter means comprises two flat membranes provided with membrane supporting means mounted liquid tight in two opposite portions of the sidewall of said filtration chamber.

25. Microconcentrator device according to claim 7, wherein said filtration chamber has the form of a flat channel having a width of the section less than 5 mm.

26. Microconcentrator device according to claim 25, wherein said filtration chamber is locally provided with a wider section arranged for receiving the tip of a pipette used for the concentrate removal.

27. Microconcentrator device according to claim 25, wherein said filtration chamber has a tapered form with an angle between two opposite sidewall portions in the range of 1°–12°.

28. Microconcentrator device according to claim 7, wherein the volume of the concentrate pocket is sized to allow concentration of 10 to 300 times of the initial sample volume.

29. Microconcentrator device according to claim 7, wherein the volume of said filtration chamber is less than 30% total volume of said sample reservoir.

* * * * *